US00PP31011P2

(12) United States Plant Patent
Bacon

(10) Patent No.: US PP31,011 P2
(45) Date of Patent: Nov. 5, 2019

(54) GRAPEVINE PLANT NAMED 'SUGRAFIFTYSIX'

(50) Latin Name: *Vitis vinifera*
Varietal Denomination: Sugrafiftysix

(71) Applicant: Sun World International, LLC, Bakersfield, CA (US)

(72) Inventor: Terry A. Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 0 days.

(21) Appl. No.: 16/350,627

(22) Filed: Dec. 11, 2018

(51) Int. Cl.
*A01H 5/08* (2018.01)
*A01H 6/88* (2018.01)

(52) U.S. Cl.
USPC ..... Plt./205

(58) Field of Classification Search
USPC ..... Plt./205
CPC ..... A01H 5/08; A01H 6/88
See application file for complete search history.

*Primary Examiner* — Annette H Para
(74) *Attorney, Agent, or Firm* — Knobbe, Martens, Olson & Bear, LLP

(57) ABSTRACT

A new and distinct grapevine variety 'Sugrafiftysix' is described. The new variety 'Sugrafiftysix' is characterized by having narrow elliptic, green berries that are very large and very firm and crisp. The berries form large clusters and ripen in mid-season, about August 17$^{th}$, in the area of Wasco, Kern County, Calif.

1 Drawing Sheet

Latin name of the genus and species claimed: *Vitis vinifera.*

Variety denomination: 'SUGRAFIFTYSIX'.

BACKGROUND AND SUMMARY OF THE INVENTION

This application relates to the discovery and asexual propagation of a new and distinct variety of grapevine, 'Sugrafiftysix', as herein described and illustrated. The new variety was first selected as breeder number 'GR560W' by Terry A. Bacon in Wasco, Kern County, Calif. in August 2015. The variety was originated by controlled hybridization.

The new variety 'Sugrafiftysix' is characterized by narrow elliptic, green berries that are very large and very firm. The vine forms large clusters and ripening begins in mid-season, about August 17, in the area of Wasco, Kern County, Calif.

The seed parent is the varietal selection 'Sugrathirtyfive' (U.S. Plant Pat. No. 20,491) and the pollen parent is the varietal selection 'GR115W' (unpatented breeding selection). The parent varieties were first crossed in May 2012. The date of first sowing was March 2013, and the date of first flowering was May 2015.

The new variety 'Sugrafiftysix' was first asexually propagated in December 2015 in Wasco, Kern County, Calif., by Terry A. Bacon using hardwood cuttings.

The new variety 'Sugrafiftysix' resembles its seed parent 'Sugrathirtyfive' in appearance and color, but the fruit of the new variety 'Sugrafiftysix' begins ripening about August 17th compared to September 1st for 'Sugrathirtyfive'. The new variety also differs from the seed parent in that the shape of the berries of the new variety is narrow elliptic, while the shape of the berries of 'Sugrathirtyfive' is broad elliptic.

The new variety 'Sugrafiftysix' differs from its pollen parent 'GR115W' in that the fruit of the new variety begins ripening about August 17th compared to September 15th for 'GR115W'. The new variety 'Sugrafiftysix' also differs from its pollen parent in that the shape of the berries is narrow elliptic, while the shape of the berries for 'GR115W' is obtuse ovate.

The berries of the new variety 'Sugrafiftysix' have a similar color to the berries of 'Autumn King' (U.S. Plant Pat. No. 16,284). However, the berries of the new variety begin ripening on August 17th compared to September 20th for 'Autumn King'. In addition, the berries of the new variety have a sweet neutral aroma with crisp-juicy texture compared to a bland neutral aroma and soft-meaty texture for 'Autumn King'. The new variety 'Sugrafiftysix' also differs from 'Thompson Seedless' (unpatented) in that the berries of the new variety have a narrow elliptic berry shape and a cluster weight of about 850 g compared to an elongated berry shape and a cluster weight of about 550 g for 'Thompson Seedless'. Additionally, 'Thompson Seedless' begins ripening earlier than 'Sugrafiftysix', on about July 27$^{th}$ compared to August 17$^{th}$ for 'Sugrafiftysix'.

The new 'Sugrafiftysix' variety has been shown to maintain its distinguishing characteristics through successive, asexual propagations by, for example, cuttings and grafting.

Variations of the usual magnitude from the characteristics described herein may occur with changes in any of a variety of factors such as growing conditions, irrigation, fertilization, pruning, management and climatic variation.

BRIEF DESCRIPTION OF THE DRAWING

The accompanying color photographic illustration shows typical specimens of the foliage and fruit of the present new grape variety 'Sugrafiftysix'. The illustration shows the upper and lower surfaces of the leaves and exterior and sectional views of the fruit. The photographic illustration was taken shortly after the fruit was picked and the colors are as nearly true as is reasonably possible in a color representation of this type.

DETAILED DESCRIPTION OF THE PREFERRED EMBODIMENT

Figure 1:
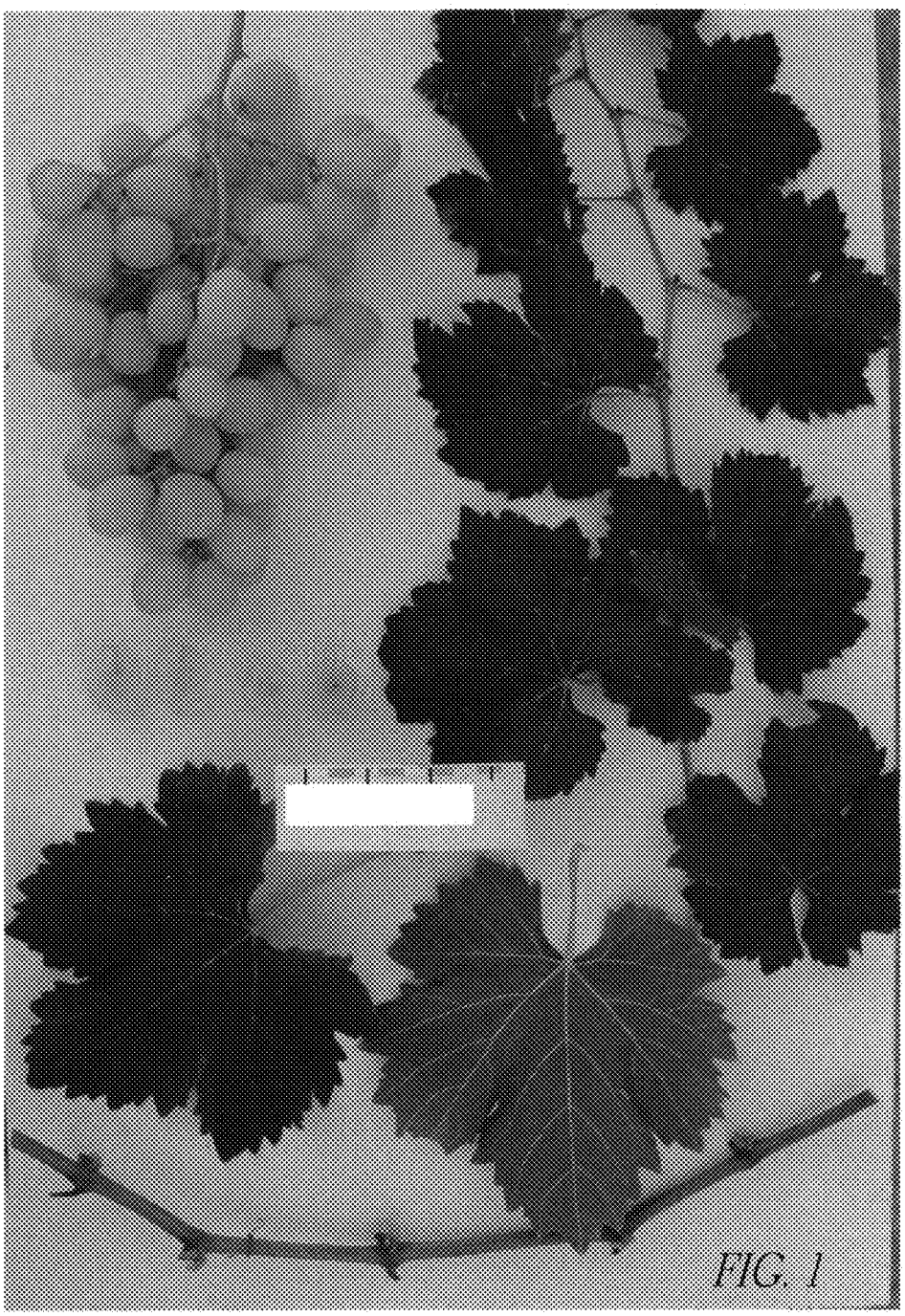

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England, 1986.

Many of the descriptive values in this specification are based on and conform to those set forth by the International Board for Plant Genetic Resources Institute Grape Descriptors (*Vitis* spp.) of 1983 and/or 1997, which was developed in collaboration with the Office International de la Vigne et du Vin (OIV) and the International Union for the Protection of New Varieties of Plants (UPOV).

The descriptive matter which follows pertains to a three year old 'Sugrafiftysix' plants grown in the vicinity of Wasco, Kern County, Calif. during 2018, and is believed to apply to plants of the variety grown under similar conditions of soil and climate elsewhere.

VINE

General: (Measurements taken on a three year old plant).

- *Vine size*.—Large. Height: Approximately 2.0 m. Width: Approximately 2.5 m.
- *Vigor*.—Vigorous.
- *Density of foliage*.—Dense.
- *Productivity*.—Very productive.
- *Crop load*.—Approximately 34 kg per vine after removing extra clusters.
- *Own root*.—Yes.
- *Training method*.—Typically spur pruned leaving 36-40 two-bud spurs.
- *Resistance*.—Average resistance and susceptibility to diseases or pests of *Vitis vinifera* species.

Trunk:

- *Shape*.—Stocky.
- *Diameter*.—Approximately 7.5 cm (at 30 cm above the soil line).
- *Straps*.—Short.
- *Surface texture*.—Medium shaggy.
- *Inner and outer bark color*.—Inner bark about Medium Greyed-Orange 166C and Medium Greyed-Orange 173C weathering to about Dark Greyed-Green 197B in the outer bark.

SHOOTS

Young shoot:

- *Form of tip*.—Half open.
- *Intensity of anthocyanin coloration of tip*.—Absent or very weak.
- *Density of prostrate hairs on tip*.—Absent or very sparse.
- *Density of erect hairs on tip*.—Absent or very sparse.
- *Color*.—About Medium Yellow-Green 144C.

Woody shoot: (Observations made in the middle third of shoot in August 2018).

- *Attitude before tying*.—Semi-drooping.
- *Growth of axillary shoots*.—Medium, approximately 17 cm to 21 cm.
- *Internode length*.—Medium, approximately 70 mm to 90 mm.
- *Width at node*.—Approximately 13 mm.
- *Cross section*.—Circular.
- *Surface texture*.—Striated.
- *Main color*.—About Medium Greyed-Orange 166C.
- *Color of dorsal side of internode*.—About Medium Greyed-Orange 166C.
- *Color of ventral side of internode*.—About Medium Greyed-Orange 166D.
- *Color of dorsal side of node*.—About Medium Yellow-Green 146D with Medium Greyed-Orange 166C.
- *Color of ventral side of node*.—About Medium Yellow-Green 146D with Medium Greyed-Orange 166C.
- *Density of erect hairs on nodes*.—Absent or Very Sparse.
- *Density of erect hairs on internodes*.—Absent or Very Sparse.
- *Density of prostrate hairs on internodes*.—Absent or Very Sparse.
- *Density of prostrate hairs on nodes*.—Absent or Very Sparse.

Tendrils:

- *Distribution on the shoot at full flowering*.—Discontinuous.
- *Thickness*.—Approximately 3 mm.
- *Color*.—About Medium Yellow-Green 144C in midsummer.
- *Form*.—Bifurcated.
- *Number of consecutive tendrils*.—Up to two.
- *Length of tendril*.—Medium, approximately 150 mm to 190 mm.

LEAVES

Young leaves:

- *Color of upper surface of first 4 distal unfolded leaves*.—About Medium Green 138B.
- *Average intensity of anthocyanin coloration of six distal leaves prior to flowering*.—Absent.
- *Density of prostrate hairs between veins at lower surface of 4th distal unfolded leaf*.—Absent or very sparse.
- *Density of erect hairs between veins at lower surface of 4th distal unfolded leaf*.—Absent or very sparse.
- *Density of prostrate hairs on veins at lower surface of 4th distal unfolded leaf*.—Absent or very sparse.
- *Density of erect hairs on veins at lower surface of 4th distal unfolded leaf*.—Absent or very sparse.

Mature leaves: (Observations made on leaves in the middle third of shoot in August 2018).

- *Average length*.—Large, approximately 125 mm.
- *Average width*.—Large, approximately 165 mm.
- *Shape of blade*.—Pentagonal.
- *Number of lobes*.—Approximately five.
- *Mature leaf profile*.—Undulate.
- *Blistering surface of blade upper surface*.—Absent or very weak.
- *Leaf blade tip*.—In the plane of the leaf.
- *Undulation of margin*.—Slight.
- *Thickness*.—Average — typical of *Vitis vinifera* species.

*Overall shape of teeth*.—Mixture of both sides straight and both sides convex.
*Length of teeth*.—Medium, ranging from about 4 mm to 10 mm.
*Ratio length/width of teeth*.—Very small, nearly 1:1.
*General shape of petiole sinus lobes*.—Half open.
*Tooth at petiole sinus*.—Absent.
*Petiole sinus limited by veins*.—Absent.
*Shape of upper lateral sinus lobes*.—Usually slightly overlapping, some closed.
*Depth of upper lateral sinuses*.—Deep, approximately 50 mm.
*Density of prostrate hairs between veins on lower surface of blade*.—Absent to very sparse.
*Density of erect hairs between veins on lower surface of blade*.—Absent to very sparse.
*Density of prostrate hairs on main veins on lower surface of blade*.—Absent to very sparse.
*Density of erect hairs on main veins on lower surface of blade*.—Absent to very sparse.
*Density of prostrate hairs on main veins on upper surface of blade*.—Absent to very sparse.
*Autumn coloration of leaves*.—Mainly about Dark Green 139A but some leaves are mixed Dark Green 138A with Dark Greyed-Purple 187A and Dark Yellow-Green 154A.

Upper leaf surface:
*Color*.—About Dark Green 139A.
*Surface texture*.—Smooth.
*Surface appearance*.—Dull.
*Anthocyanin coloration of main veins*.—Absent or very sparse.

Lower leaf surface:
*Color*.—About Medium Green 138B.
*Surface texture*.—Smooth.
*Surface appearance*.—Dull.
*Anthocyanin coloration of main veins*.—Absent or very sparse.

Petiole:
*Length of petiole*.—Approximately 70 mm.
*Diameter*.—Approximately 4 mm.
*Length of petiole compared to middle vein*.—Much shorter, 70 mm petiole compared to 125 mm middle vein.
*Density of prostrate hairs on petiole*.—Absent.
*Density of erect hairs on petiole*.—Absent.
*Color*.—About Medium Yellow-Green 147C.

Buds:
*Shape*.—Conical.
*Size*.—Medium, approximately 3 mm wide and 4 mm long.
*Position*.—Slightly held out.
*Bud fruitfulness*.—Good fertility, mostly fruitful in $3^{rd}$ to $5^{th}$ bud position with 1 to 2 clusters per shoot.
*Time of bud burst*.—Medium, approximately March $18^{th}$, for the region of the Southern San Joaquin Valley, Calif.

FLOWERS

General:
*Flower type*.—Fully developed stamen and fully developed gynoecium.
*Position of first flowering node*.—Usually $3^{rd}$ to $5^{th}$ node of current season growth.
*Number of inflorescences per shoot*.—Average 1.5.
*Time of full bloom*.—Medium for the area of the Southern San Joaquin Valley, Calif. Approximately May $7^{th}$.

FRUIT

General:
*Ripening period*.—Midseason, beginning about August $17^{th}$ with mid-ripe about August $22^{nd}$ in the area of the Southern San Joaquin Valley, Calif.
*Use*.—Fresh market.
*Storage quality*.—Excellent.

Cluster:
*Form*.—Conical, shouldered.
*Cluster size* (*peduncle excluded*).—Large.
*Cluster length* (*peduncle excluded*).—Approximately 230 mm.
*Cluster width*.—Approximately 130 mm.
*Cluster weight*.—Approximately 850 g.
*Cluster density*.—Medium, loose and full.
*Number of berries*.—Approximately 80.

Peduncle:
*Length*.—Medium, approximately 20 mm.
*Diameter*.—Approximately 6 mm.
*Lignification of peduncle*.—Weak.
*Color*.—About Medium Yellow-Green 146C.

Berry:
*Size*.—Very large, approximately 10.5 g.
*Dimensions*.—Longitudinal axis: Approximately 28 mm. Horizontal axis: Approximately 23 mm.
*Uniformity of size*.—Uniform.
*Shape*.—Narrow elliptic.
*Cross section*.—Circular.
*Skin color* (*without bloom*).—About Medium Yellow-Green 144B to Medium Yellow-Green 146C.
*Flesh color*.—About Medium Yellow-Green 144C.
*Anthocyanin color of flesh*.—Absent or very weak.
*Bloom* (*cuticular wax*).—Medium.
*Pedicel length*.—Approximately 7 mm.
*Pedicel thickness*.—Medium, approximately 1.8 mm.
*Berry separation from pedicel*.—Moderately easy.
*Seed traces*.—Berries contain 1 to 3 about Medium Greyed-White 156B rudimentary soft seed traces per berry.
*Berry firmness*.—Very firm.
*Flesh juiciness*.—Juicy.
*Flesh texture*.—Crisp.
*Particular flavor*.—Low-acid with no particular aroma.
*Refractometer test*.—Approximately 18 Brix.
*Juice ph*.—Approximately 3.6.
*Titratable acidity*.—Approximately 0.40%.
*Brix:acid ratio*.—Approximately 45.

Skin:
*Skin thickness*.—Medium, about 175 μm.
*Skin texture*.—Smooth.
*Skin reticulation*.—Absent.
*Skin tenacity*.—Tenacious to flesh.
*Skin tendency to crack*.—Low.
*Skin sensitivity to sunburn*.—None or very low.

What is claimed is:

1. A new and distinct variety of grapevine as herein illustrated and described.

* * * * *